United States Patent [19]

Burkoth

[11] Patent Number: 5,189,986
[45] Date of Patent: Mar. 2, 1993

[54] VETERINARY TRANSDERMAL ACTIVE AGENT DELIVERY DEVICE

[75] Inventor: Terry L. Burkoth, Palo Alto, Calif.
[73] Assignee: Alza Corporation, Palo Alto, Calif.
[21] Appl. No.: 764,436
[22] Filed: Sep. 23, 1991
[51] Int. Cl.$^5$ .............................................. A01K 13/00
[52] U.S. Cl. ..................................................... 119/156
[58] Field of Search .................. 119/156; 40/300, 301, 40/302; 604/304, 308; 606/116, 117

[56] References Cited

U.S. PATENT DOCUMENTS

| | | | |
|---|---|---|---|
| 3,333,586 | 8/1967 | Bellis et al. | 604/308 |
| 3,598,122 | 8/1971 | Zaffaroni | 128/268 |
| 3,598,123 | 8/1971 | Zaffaroni | 128/268 |
| 3,756,200 | 9/1973 | Ohlhausen | 119/156 |
| 3,942,480 | 3/1976 | Hair et al. | 119/156 |
| 3,949,708 | 4/1976 | Meeks | 119/156 |
| 4,026,290 | 5/1977 | Brooker et al. | 128/260 |
| 4,059,074 | 11/1977 | Füer et al. | 119/156 |
| 4,144,317 | 3/1979 | Higuchi et al. | 424/21 |
| 4,184,453 | 1/1980 | Ritchey | 119/156 |
| 4,265,876 | 5/1981 | Feakins | 424/28 |
| 4,286,592 | 9/1981 | Chandrasekaran | 128/260 |
| 4,297,995 | 11/1981 | Golub | 604/308 |
| 4,314,557 | 2/1982 | Chandrasekaran | 128/260 |
| 4,359,015 | 11/1982 | Ritchey | 119/156 |
| 4,366,777 | 1/1983 | Akhavein et al. | 119/156 |
| 4,379,454 | 4/1983 | Campbell et al. | 604/897 |
| 4,425,874 | 1/1984 | Child | 119/156 |
| 4,428,327 | 1/1984 | Steckel | 119/156 |
| 4,495,898 | 1/1985 | Akhavein et al. | 119/156 |
| 4,506,630 | 3/1985 | Hair | 119/156 |
| 4,544,547 | 10/1985 | von Bittera et al. | 424/14 |
| 4,562,794 | 1/1986 | Speckman | 119/156 |
| 4,568,343 | 2/1986 | Leeper et al. | 604/896 |
| 4,579,085 | 4/1986 | McGuire | 119/156 |
| 4,581,834 | 4/1986 | Zatkos et al. | 40/301 |
| 4,606,478 | 8/1986 | Hack et al. | 222/187 |
| 4,612,877 | 9/1986 | Hayes et al. | 119/156 |
| 4,674,445 | 6/1987 | Cannelongo | 119/156 |
| 4,694,781 | 9/1987 | Howe et al. | 119/156 |
| 4,697,549 | 10/1987 | Hair | 119/156 |
| 4,718,374 | 1/1988 | Hayes | 119/156 |
| 4,721,064 | 1/1988 | Denk et al. | 119/156 |
| 4,750,284 | 6/1988 | Parry et al. | 40/301 |
| 4,878,456 | 11/1989 | Howe | 119/156 |
| 4,885,855 | 12/1989 | Marks, Sr. et al. | 40/301 |
| 5,016,369 | 5/1991 | Parry | 119/156 |

FOREIGN PATENT DOCUMENTS

| | | |
|---|---|---|
| 0376143 | 4/1990 | European Pat. Off. |
| 2062552A | 5/1981 | United Kingdom. |
| 82/01639 | 5/1982 | World Int. Prop. O. |
| 90/13270 | 11/1990 | World Int. Prop. O. |

OTHER PUBLICATIONS

Pitman, Ian H. and Rostas, Susan J. "Journal of Pharmaceutical Sciences", 70(11), pp. 1181–1193 (1981).
Pitman, Ian H. and Rostas, Susan J. "Journal of Pharmaceutical Sciences", 71(4), pp. 427–430 (1982).

Primary Examiner—Gene Mancene
Assistant Examiner—Todd E. Manahan
Attorney, Agent, or Firm—Jean M. Duvall; Jacqueline S. Larson; Steven F. Stone

[57] ABSTRACT

The present invention is directed to the veterinary transdermal application of an active agent to an animal. More particularly, the invention is directed to an active agent dispenser or apparatus attachable to the ear of an animal for the transdermal delivery of an active agent to the animal. The dispenser comprises an ear tag component and a transdermal device component, wherein the transdermal component is held tightly in active agent-transmitting relation to the ear of an animal by the ear tag component.

7 Claims, 2 Drawing Sheets

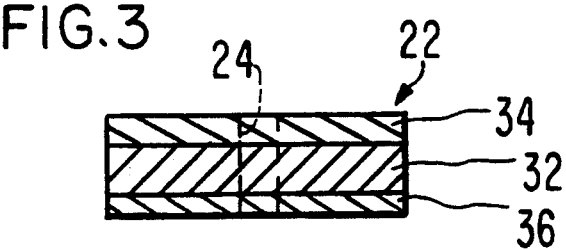
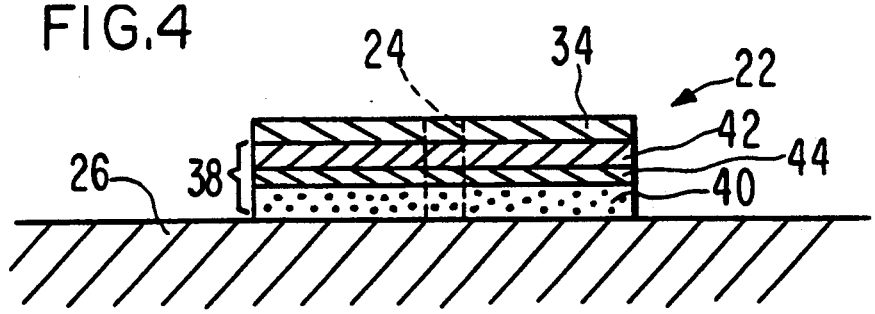
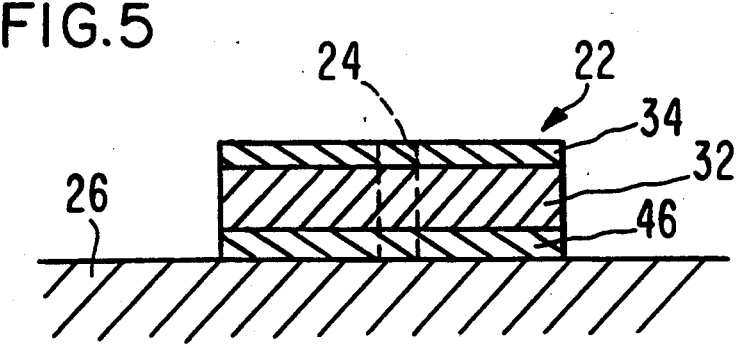

VETERINARY TRANSDERMAL ACTIVE AGENT DELIVERY DEVICE

The present invention relates generally to animal husbandry and more particularly to apparatus and techniques for administering veterinary medicaments through the skin.

BACKGROUND OF THE INVENTION

Identification animal ear tags for cattle, hogs, sheep and the like are in widespread use. The most popular forms of these tags comprise two components formed of plastic or other resilient material, the male component having a pointed pin, spike or rivet of hard plastic material which is adapted to be forced through an animal ear and the female component which can be urged over the pointed end of the rivet to retain the male component in position on the ear. The means of identification, i.e., the tag itself, can be attached to or integrally formed with either or both components of the two-component tag. U.S. Pat. Nos. 4,544,547, 4,581,834, and 4,694,781; U.K. Pat. GB 2 062 552: and PCT patent publication WO 82/01639 describe exemplary two-component tags.

As ear identification tags for animals are increasingly used, various techniques also have been devised for using such tags to topically release agents such as insecticides, insect repellents or animal repellents, either through separately applied tags or by adding a carrier of some type to the identification ear tag. However, these all have certain problems or drawbacks in addition to being for topical rather than transdermal delivery of agent. Those ear tags where the tag itself is made of a material impregnated with an insecticide, such as disclosed in U.S. Pat. Nos. 4,184,453 and 4,265,876 for example, pose the problem that within a relatively short period of time the insecticide is used up. Where the tags have been adapted to include replenishable insecticide devices (examples of which are disclosed in U.S. Pat. Nos. 3,949,708, 4,425,874, 4,562,794, 4,694,781 and 4,697,549), the tags themselves are of special construction to accommodate the the different insecticide dispensers. With insecticide carriers which are wrapped around a portion of the tag to fasten upon themselves, removal and installation of the carriers is cumbersome. Examples of such carriers are described in U.S. Pat. Nos. 4,366,777 and 4,495,898. Additionally, all are for topical rather than transdermal delivery of an active agent.

Transdermal drug delivery in veterinary applications is discussed by Pitman and Rostas in Journal of Pharmaceutical Sciences, 70(11):1181-1193 (1981), and 71(4):427-430 (1982). A few techniques and devices are known for administering medicaments through the skin for veterinary use. One example of such a technique is described in U.S. Pat. No. 4,026,290, which suggests attachment of a device to the ears or tail of an animal for applying a drug. Another example is described in EP application 376,143, which describes a device which is wrapped completely around the ear.

Transdermal drug delivery devices for placement by adhesive means onto the skin are well-known for use with humans. Examples of such devices are described in U.S. Pat. Nos. 3,598,122, 3,598,123, 4,379,454, 4,286,592, 4,314,557 and 4,568,343, for example, all of which are incorporated herein by reference. However, such devices are not useful for animals. Retention is not reliable because of exposure to weather or of animal behavior such as grooming. Also, locations free of hair growth to allow the use of aggressive adhesive are rare. Moreover, any dramatic change in animal handling practices required of livestockmen would be met with resistance.

Accordingly, it is desirable to provide an active agent transdermal delivery device which is practical and simple to use, can be manufactured economically, may be used in conjunction with a standard unmodified ear identification tag and which is easy to apply and easy to remove and is readily removable without requiring removal of the identification tag. It is also desirable to provide a device for transdermal delivery without altering animal handling practices or increasing cost.

SUMMARY OF THE INVENTION

The present invention is directed to the veterinary transdermal application of an active agent to an animal. More particularly, the invention is directed to an active agent dispenser or apparatus attachable to the ear of an animal for the transdermal delivery of an active agent to the animal, where the dispenser comprises:

a) an ear tag component which includes a front plate, a rear plate and a pin or rivet adapted to interconnect the front and rear plates upon penetrating the animal's ear; and b) a transdermal device component which includes a backing layer, a matrix which includes the active agent to be delivered, and an opening extending through the surface of the device for receiving the rivet of the ear tag component;

wherein, the transdermal device component is held tightly in active agent-transmitting relation with the skin of the ear of the animal by the ear tag component.

The present invention is also directed to the use of such dispensers for delivering an active agent transdermally to animals.

BRIEF DESCRIPTION OF THE DRAWINGS

FIG. 3 is a cross-sectional view of one embodiment of the transdermal device component which may be used in accordance with the present invention.

FIG. 4 is a cross-sectional view of another embodiment of the transdermal device component which may be used in accordance with the invention.

FIG. 5 is a cross-sectional view of yet another embodiment of the transdermal device component which may be used in accordance with the present invention.

DETAILED DESCRIPTION OF PREFERRED EMBODIMENTS

Figure 1:
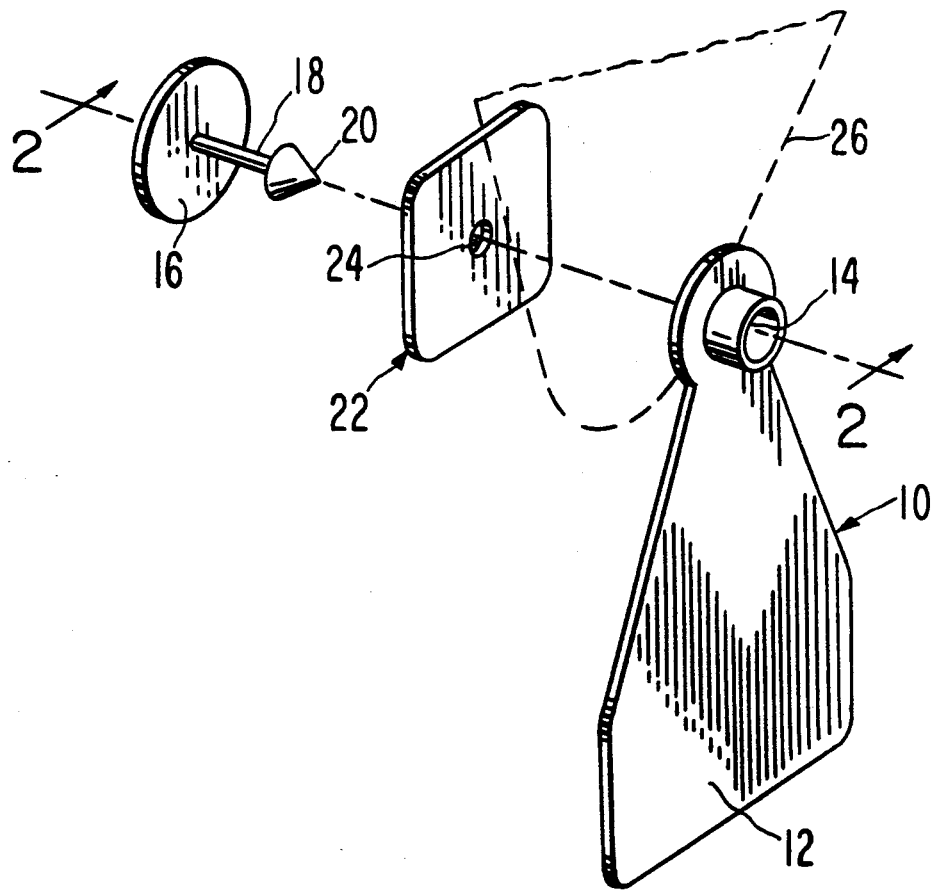
FIG. 1 is a front perspective view of one embodiment of the dispensing system of the invention.

This invention utilizes principles of transdermal drug delivery and of ear tag technology to provide a novel system for effectively administering veterinary active agents to animals.

In the drawings, the same reference numbers are used throughout the different figures to designate the same or similar components.

FIG. 1 shows one embodiment of the dispensing system of the present invention. The ear tag component of the present dispenser system is illustrated as a conventional two-piece livestock ear tag 10 having a front plate 12, which in this embodiment is enlarged to provide identification means, and a rear plate 16. Rear plate 16 has a pin or rivet extending therefrom, which rivet is comprised of an elongated shaft 18 terminating in a flared, pointed tip 20. The transdermal device component 22 of the dispenser system has a hole or opening 24 extending through the transdermal device for receiving the rivet of the ear tag component.

Figure 2:
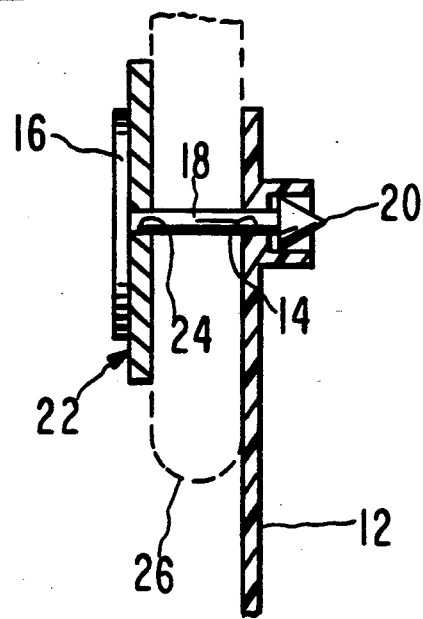
FIG. 2 is a cross-sectional view of a portion of the dispensing system shown in FIG. 1.

In practice, to attach the dispenser system of the invention to the ear of an animal (denoted by dotted line 26 in the Figure), pointed tip 20 of the rivet is first passed through opening 24 of transdermal component 22, then through the ear 26 of the animal and through the hole or opening 14 of the front plate 12 of the ear tag component. Methods and tools for attaching ear tags are well known in the art. Rear plate 16 holds the transdermal component 22 tightly against the ear 26 to place the transdermal component in active agent-transmitting relation with the skin of the ear of the animal. This is most clearly illustrated in FIG. 2, which is a cross-section along line 2—2 of the system of FIG. 1. Alternatively, transdermal device component 22 may be placed between front plate 12 and ear 26 rather than between the ear and rear plate 16. In a preferred embodiment, the transdermal component 22 is placed against the inside surface of the ear, where it is somewhat more protected from the weather and is against less hairy skin to provide improved skin absorption of the active agent.

It is to be understood that two-component ear tags other than the one shown in FIG. 1 may be used in the present invention, as long as the front and/or rear plate is sufficient to hold the transdermal device component in active agent-transmitting relation with the skin of the animal.

One embodiment of the transdermal delivery device component that can be used in the present invention is illustrated in FIG. 3. In FIG. 3, transdermal component 22 is comprised of an active agent-containing reservoir ("drug reservoir") 32 which is preferably in the form of a matrix containing the active agent and any additives, such as a permeation enhancer, dispersed therein. A backing layer 34 is provided adjacent one surface of drug reservoir 32. Backing layer 34 is impermeable to the active agent and any other components in drug reservoir 32. A strippable or removeable liner 36 is also provided with transdermal component 22 and is removed prior to application of component 22 to the skin of the ear. The dashes indicate the opening 24 extending through the layers of the transdermal device component, which opening may conveniently be punched from the device after the device has been manufactured.

FIG. 4 illustrates another embodiment of the transdermal device component 22, shown in place upon the animal's ear 26. In this embodiment, the transdermal therapeutic delivery component 22 comprises a multilaminate drug formulation/permeation enhancer reservoir 38 having at least two zones 40 and 42. Zone 40 consists of a drug reservoir substantially as described with respect to FIG. 3. Zone 42 comprises a permeation enhancer reservoir which is preferably made from substantially the same matrix as is used to form zone 40. Zone 42 comprises permeation enhancer dispersed throughout and is substantially free of any undissolved drug. A rate-controlling membrane 44 for controlling the release rate of the enhancer from zone 42 to zone 40 is placed between the two zones. A rate-controlling membrane (not shown) for controlling the release rate of the enhancer from zone 40 to the skin may also optionally be utilized and would be present between the skin 26 of the ear and zone 40.

The rate-controlling membrane may be fabricated from permeable, semipermeable or microporous materials which are known in the art to control the rate of agents into and out of delivery devices and having a permeability to the permeation enhancer lower than that of zone 40. Suitable materials include, but are not limited to, polyethylene, polyvinyl acetate and ethylene vinyl acetate copolymers.

An advantage of the device described in FIG. 4 is that the drug-loaded zone 40 is concentrated at the skin surface rather than throughout the entire mass of the reservoir 38. This functions to reduce the amount of drugs in the device while maintaining an adequate permeation enhancer supply.

Superimposed over the drug formulation/enhancer reservoir 38 of device 22 is an impermeable backing layer 34 as described above with respect to FIG. 3. In addition, a strippable liner (not shown) would preferably be provided on the device prior to use as described with respect to FIG. 3 and removed prior to application of the device component to the animal's ear 26.

In the embodiments of FIGS. 3 and 4, the carrier or matrix material has sufficient viscosity to maintain its shape without oozing or flowing. If, however, the matrix or carrier is a low-viscosity flowable material, the composition can be fully enclosed in a pouch or pocket formed between the impermeable backing and a permeable or microporous skin-contacting membrane, as known to the art from U.S. Pat. No. 4,379,454 (noted above), for example, or between the impermeable backing and the rate-controlling membrane, if present.

Another example of an embodiment of the transdermal delivery device component is illustrated in FIG. 5. In FIG. 5, transdermal delivery device component 22 comprises a drug reservoir 32 containing the active agent and any additives. Reservoir 32 is preferably in the form of a matrix containing the drug dispersed therein. Reservoir 32 is sandwiched between a backing layer 34, which is impermeable to the drug and any other components in reservoir 32, and a rate-controlling membrane 46. In FIG. 5, the drug reservoir 32 is formed of a material, such as a rubbery polymer, that is sufficiently viscous to maintain its shape. The dashes indicate the opening 24. A strippable liner (not shown) is normally provided along the exposed surface of rate-controlling membrane 46 and is removed prior to application of device 22 to the ear 26.

In an optional embodiment of the present invention, a contact adhesive layer may be present on the skin-proximal surface of the transdermal device component to assist in maintaining the transdermal component in active agent-transmitting relation with the skin of the animal's ear. The adhesive should be chosen so that it is compatible and does not interact with any of the active agent or other components of the transdermal device. Where it is desired to remove the transdermal device component from the ear without disturbing the ear tag component, the adhesive should not be so strong as to inhibit such removal.

Various materials suited for the fabrication of the various layers of the transdermal device components of FIGS. 3, 4 or 5 are known in the art or are disclosed in the aforementioned transdermal device patents previously incorporated herein by reference.

The matrix making up the active agent reservoir can be a gel or a polymer. Suitable materials should be compatible with the agent and any other components in the system. Suitable matrix materials include, without limitation, natural and synthetic rubbers or other polymeric material, thickened mineral oil, or petroleum jelly, for example. The matrix is preferably polymeric and is more preferably an anhydrous polymer. A preferred embodiment according to this invention is fabricated from an ethylene vinyl acetate (EVA) copolymer, of the type described in U.S. Pat. No. 4,144,317, and is preferably selected from those EVAs having a vinyl acetate (VA) content in the range of about 9 to 60%, preferably about 28 to 60% VA.

In addition to an active agent, the matrix may also contain permeation enhancers, stabilizers, dyes, pigments, inert fillers, tackifiers, excipients and other conventional components of transdermal delivery devices as are known in the art.

In a presently preferred embodiment, the transdermal device component is made of materials which have the ability to deform or tear for easy removal of the transdermal component without disturbing the ear tag component. This is useful when it is desired to terminate application of the active agent while retaining the ear tag itself on the animal. Termination of application may be desirable to prevent residues of the drug from remaining in the tissues of the animal or in food products produced by the animal, such as milk. Removal of the transdermal component and thus termination of application of the drug may be precisely timed. For example, removal may take place at a predetermined length of time before slaughter of the animal for preventing more than a threshold amount of the residue of the drug from remaining in the slaughtered animal. Or, the steps of applying and then removing the transdermal component is done at preselected times which are synchronized, such as fertility synchronization of a herd.

The transdermal device component may be of any shape, such as for example round, square, oval or rectangular. The size also may vary, but is generally of from about 10 cm² to about 100 cm². The size and shape of the transdermal component will be chosen to conform to the animal being treated, the skin-permeating characteristics of the active agent being delivered, and the length of time during which the agent is to be applied.

The terms "active agent" and "drug" are interchangeable as used herein. Active agents or drugs which can be delivered according to the present invention may be any suitable agent and may be selected from, but are not limited to, growth regulators and growth promoters, fertility agents, medicaments for the control of ovulation in breeding animals, nutritional supplements such as vitamins and trace elements, anthelmintics, and anti-inflammatory agents.

The active agent can be present in the invention in the various chemical and physical forms such as uncharged molecules, molecular complexes, and pharmacologically acceptable acid addition and base addition salts. For acidic compounds, salts of metals, amines or organic cations can be used. Derivatives of agents such as esters, ethers and amides can be used. An active agent can be used alone or mixed with other active agents.

The list of active agents recited above is given only to illustrate the types of active agents which are suitable for use in practicing the invention, and is not intended to be exhaustive.

The amount of active agent present in the therapeutic device component will be that amount necessary to deliver a therapeutically effective amount of the agent to achieve the desired result at the site of application. In practice, this will vary and depends on many factors, such as the particular agent chosen; the minimum necessary dosage of the agent; the severity of the condition; the desired effect; the permeability of the matrix, and of the rate-controlling membrane, if present; and the length of time during which the device will be fixed to the skin. Since the active agents are to be released over a period of more than one day, there is, in fact, no upper limit to the maximum amounts of the agent present in the device. The minimum amount of the active agent is determined by the requirement that sufficient quantities of agent must be present in the device to maintain the desired rate of release over the given period of application.

Methods of making the transdermal device component are well known in the art and can be made following the procedures in, for example, the transdermal drug delivery device U.S. patents previously incorporated herein by reference.

Although different embodiments of the invention have been illustrated in the various figures of the drawings and have been described in the description, these embodiments are to be considered as illustrative only of the invention and not as limiting. Various changes and modifications will occur to those skilled in the art without departing from the scope of the invention as defined by the claims.

What is claimed is:

1. An active agent dispensing system attachable to the ear of an animal for the transdermal delivery of an active agent to the animal, the dispensing system comprising:
    (a) an ear tag component comprising:
        (i) a front plate,
        (ii) a rear plate, and
        (iii) a pin or rivet adapted to interconnect the front and rear plates upon penetrating the animal's ear; and
    (b) a transdermal device component located between the front plate and the ear or between the rear plate and the ear comprising:
        (i) a backing layer,
        (ii) a matrix comprising the active agent to be delivered, and
        (iii) an opening extending through the transdermal device for receiving the rivet of the ear tag component;
    wherein, the transdermal device component is held in active agent-transmitting relation with the skin of the ear of the animal by the ear tag component.

2. A dispensing system according to claim 1 wherein the transdermal device component further comprises a rate-controlling membrane.

3. A dispensing system according to claim 1 wherein the active agent is selected from the group consisting of growth regulators, growth promoters, fertility agents, medicaments for the control of ovulation in the breeding animals, nutritional supplements, anthelmintics, and anti-inflammatory agents.

4. An method for delivering an active agent transdermally to an animal, which method comprises attaching an active agent dispensing system to the ear of an animal, the dispensing system comprising:
    (a) an ear tag component comprising:
        (i) a front plate,
        (ii) a rear plate, and
        (iii) a pin or rivet adapted to interconnect the front and rear plates upon penetrating the animal's ear; and (b) a transdermal device component located between the front plate and the ear or between the rear plate and the ear comprising:
  (i) a backing layer,
  (ii) a matrix comprising the active agent to be delivered, and
  (iii) an opening extending through the transdermal device for receiving the rivet of the ear tag component;

wherein, the transdermal device component is held in active agent-transmitting relation with the skin of the ear of the animal by the ear tag component.

5. A method according to claim 4 wherein the transdermal device component further comprises a rate-controlling membrane.

6. A method according to claim 4 wherein the transdermal device component is held in active agent-transmitting relation with the skin of the inner ear of the animal.

7. A method according to claim 4 wherein the active agent is selected from the group consisting of growth regulators, growth promoters, fertility agents, medicaments for the control of ovulation in breeding animals, nutritional supplements, anthelmintics, and anti-inflammatory agents.

* * * * *